United States Patent [19]
McCague et al.

[11] Patent Number: 5,910,601
[45] Date of Patent: Jun. 8, 1999

[54] CHIRAL NITRILES, THEIR PREPARATION AND THEIR USE FOR THE MANUFACTURE OF VERAPAMIL AND ANALOGUES

[75] Inventors: Raymond McCague, Cambridgeshire; Shouming Wang, Cambridge, both of United Kingdom

[73] Assignee: Darwin Discovery Limited, United Kingdom

[21] Appl. No.: 08/624,431

[22] PCT Filed: Sep. 26, 1994

[86] PCT No.: PCT/GB94/02091

§ 371 Date: Mar. 27, 1996

§ 102(e) Date: Mar. 27, 1996

[87] PCT Pub. No.: WO95/09150

PCT Pub. Date: Apr. 6, 1995

[51] Int. Cl.⁶ ..................... C07C 255/07; C07C 255/33; C07C 255/42
[52] U.S. Cl. ............................................................. 558/354
[58] Field of Search ............................................. 558/354

[56] References Cited

FOREIGN PATENT DOCUMENTS

| 0231003 | 8/1987 | European Pat. Off. . |
| 0434093 | 6/1991 | European Pat. Off. . |
| 2059923 | 6/1972 | Germany . |
| 9316035 | 8/1993 | WIPO . |

OTHER PUBLICATIONS

*Hackh's Chemical Dictionary*, J. Grant, Ed. (1969), McGraw–Hill Publisher, Inc.; pp. 432–433).

*Primary Examiner*—Johann Richter
*Assistant Examiner*—Jane C. Oswecki
*Attorney, Agent, or Firm*—Saliwanchik, Lloyd & Saliwanchik

[57] ABSTRACT

The subject invention concerns a process for preparing a single enantiomer, either R or S, of R'—NH—(CH$_2$)$_3$—C(Ar)(CN)—R. The process is particularly useful for preparing verapamil, and analogues thereof, in single enantiomeric form.

7 Claims, No Drawings

CHIRAL NITRILES, THEIR PREPARATION AND THEIR USE FOR THE MANUFACTURE OF VERAPAMIL AND ANALOGUES

This application is a 371 of PCT/GB94/02091 of Sep. 26,1994

FIELD OF THE INVENTION

This invention relates to chiral compounds. In particular, it relates to a process for the manufacture of verapamil and analogues thereof, more particularly the manufacture of the single enantiomers thereof, and intermediates in that process.

BACKGROUND OF THE INVENTION

Verapamil is presently in clinical use as the racemate and is used extensively for treatment of hypertension. The (S)-isomer has the majority of the calcium channel antagonist activity, see DE-A-2059923, whilst the (R)-isomer differs in having sodium channel and other cell-pump actions in addition to a higher bioavailability, with slower clearance rate. For the treatment of hypertension, the (S)-isomer may provide a safer treatment than the racemate, with an extended therapeutic window. The (R)-isomer may be of benefit for the treatment of multidrug resistance in cancer chemotherapy, see J.F. Eliason, H. Ramuz and F. Kaufmann, Int. J. Cancer (1990) 46: 113–117; in this case hypotensive action by admixture with (S)-isomer would be undesirable. The preferential use of one of the isomers for migraine treatment is also possible, see S.J. Peroutka, Ann. Neurol. (1988) 23: 500–504.

The preparation of the single enantiomers of verapamil is a difficult chemical problem. DE-A-3723654 discloses that the isomers have been separated by resolution with, for example, binaphthol bis (dihydrogen phosphate), but this would appear to be an expensive process. Similarly, the resolution of a racemic carboxylic acid precursor with brucine, as disclosed in DE-A-2059923, and the multi-step process thereafter, does not look attractive for bulk manufacture, nor does a lengthy synthesis from the enantiomers of propane-1,2-diol, see L.J. Theodore and W.L. Nelson, J. Org. Chem. (1987) 52: 1309–1315, or separation of the final product by chromatography, see JP-A-03027326.

SUMMARY OF THE INVENTION

According to a first aspect of the present invention, a process for preparing a substantially single enantiomer (R or S) of

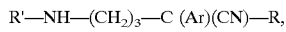

(I)

the process comprising reacting together

R—CH(Ar)—CN and X—(CH$_2$)$_3$—A to give

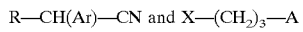

(II)

reacting command II with R'NH$_2$ to give

(III)

and resolving command III into a substantially single enantiomer thereof, wherein Ar is aryl, R and R' are each independently C$_{1-20}$ alkyl, X is a halo atom and A is a leaving group which, upon reaction of R—CH(Ar)—CN and X—(CH$_2$)$_3$—A leaves X—(CH$_2$)$_3$—A as A$^-$ and the resolution is carried out using a chiral acid.

According to a second aspect of the present invention, a process for preparing a substantially single enantiomer (R or S) of a compound of the formula

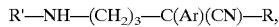

(IV)

comprises carrying out the process according to the first aspect of the invention and reacting the product thereof with Ar'—(CH$_2$)$_2$—A', wherein Ar' is aryl and A' is a leaving group which, upon reaction of Ar'—(CH$_2$)$_2$—A' with the product of the first aspect of the invetnion, leaves Ar'(CH$_2$)$_2$—A' as A'$^-$.

According to a third aspect of the present invention, a process for preparing a substantially single enantiomer (R or S) of verapamil comprises carrying out the process according to the second aspect of the invention, wherein Ar and Ar' are both 3,4-dimethoxyphenyl, R is isopropyl and R' is methyl.

Resolution of CH$_3$—NH—(CH$_2$)$_3$—C(Ar)(CN)—CH(CH$_3$)$_2$, Ar being 3,4-dimethoxyphenyl, is relatively easy compared with resolution of verapamil. For example, the novel resolution can directly achieve around 90%, or greater, enantiomeric excess, and after recrystallisation this may be increased to 99%, or greater, enantiomeric excess.

Apart from ease, a further benefit of resolution of CH$_3$—NH—(CH$_2$)$_3$—C(Ar)(CN)—CH(CH$_3$)$_2$, and its subsequent conversion to verapamil, over resolution of verapamil itself is that, given the inability to utilise both enantiomers of verapamil (which are not readily interconvertible), the amount of waste enantiomer will be reduced.

DESCRIPTION OF THE INVENTION

The process of the invention is suitable for the manufacture of a wide range of chiral compounds having Ar, Ar' and R as defined above. Preferably, the process is for preparing verapamil and analogues thereof, such as emopamil (Ar=Ar'=phenyl, R=isopropyl, R'=methyl), gallopamil (Ar=3,4,5-trimethoxyphenyl, Ar'=3,4-dimethoxyphenyl, R=isopropyl, R'=methyl), devapamil (Ar =3,4-dimethoxyphenyl, Ar'=3-methoxyphenyl, R=isopropyl, R'=methyl), mepamil (Ar=2-methylphenyl, Ar'=3,4-dimethoxyphenyl, R=n-dodecyl, R'=methyl), ronipamil (Ar=Ar'=phenyl, R=n-dodecyl, R'=methyl), dagapamil (Ar=3,4,5trimethoxyphenyl, Ar'=3-methoxyphenyl, R=n-dodecyl, R'=methyl), anapamil (Ar=3-methoxyphenyl, Ar'=phenyl, R=n-dodecyl, R'=methyl), etc.

Preparation of R—CH(Ar)—CN follows similar chemistry to that for verapamil. Resolution of R'—NH—(CH$_2$)$_3$—C(Ar)(CN)—R (compositiom III) is typically carried out with a derivative of tartaric acid, such as is produced by acylation at at least one of its hydroxyl groups, preferably di-o, o'-toluyltartaric acid, or with lithocholic acid or (R)-α-methoxy-2-(trifluoromethyl)phenylacetic acid. conversion of the resolved compound to verapamil, or the respective analogue thereof, is by standard chemical steps.

The following Example illustrates the invention.

EXAMPLE a) Preparation of 5-Chloro-2-(3,4-dimethoxyphenyl)-2-isopropylpentanenitrile 2-(3,4-dimethoxyphenyl)-3-methylbutanenitrile (1.21 g, 5.52 mmol) was added to a suspension of sodium amide (0.59 g, 14.4 mmol) in toluene (12 ml). The mixture was then heated to reflux for 2 hours before the addition of 1-chloro-3-iodopropane (0.9 ml, 8.3 mmol). The mixture was cooled to room temperature over 80 minutes, and worked up by addition of water. The product was extracted with methyl-t-butyl ether (MTBE). After usual work-up, including drying the organic extract using $MgSO_4$ and concentrating under reduced pressure the product was purified on column chromatography eluting with (ethyl acetate: light petroleum (b.p. 40–60° C.) =1:2), to give 1.4 g (82% yield) of the required product.

b) Preparation of 2-(3,4-Dimethyoxyohenyl)-2-isopropyl-5-(methylamino)pentanenitrile Into a sealed tube were placed the crude 5-chloro-2-(3, 4-dimethoxyphenyl)-2-isopropylpentanenitrile from above (0.879 g, 2.97 mmol), in absolute ethanol (4 ml), $K_2CO_3$) (1.245 g, 8.92 mmol), NaI (0.05 g), and methylamine (1.85 ml, 33% in absolute ethanol). The mixture was then heated at 100° C. for over 3 days, and the volatiles were removed on a rotary evaporator. The residue was extracted with diethyl ether. The combined organics were washed with water, then acidified with 2N hydrochloric acid. The organic phase was further extracted with 2N HCl (3×50 ml).

The combined acidic aqueous phase was then basified with 48% NaOH solution at 0° C. The product was then extracted out with diethyl ether. Usual work-up, including drying the organic extract using $MgSO_4$ and concentrating under reduced pressure gave the desired product in essentially pure form (0.62g, 71%).

c) Resolution of Methylamino Intermediate

The racemic methylamino intermediate (0.62 g, 2.1 mmol) was dissolved in methanol (2.5 ml) at room temperature, to which was added a solution of di-o,o'-toluyl-D-tartaric acid monohydrate (0.88 g, 2.1 mmol) in methanol (1.8 ml). The mixture was then cooled to 10–15° C. MTBE (4 ml) was then added to the above mixture in four equal portions. After gentle stirring the solid salt began to appear slowly. The stirring was continued for about six hours, and then the mixture was left standing for 3 days. The solid was then filtered off, washed with MTBE (4×1 ml), and dried under vacuum, giving the diastereomeric salt (0.43 g, 29%) with an ee of 93%, S. (ee was determined by eluting the p-toluyl amide derived from the methylamino intermediate and p-toluyl chloride on to a chiral cel O.J.Column, 10%, iPA/heptane 90%).

The solid salt was then dissolved in MeOH (3.4 ml) under gentle heating, and slowly cooled to room temperature. A trace amount of MTBE was added to the solution to facilitate recrystallisation. The salt obtained was then filtered, washed with MTBE (3.7 ml) and dried under vacuum to give the first crop (2.6 g, 61% yield, 99.96% ee, S,$(\alpha)_D$ =(+)70.2 (c=i, abs. EtOH).

The combined liquors were left at room temperature to give second crop (0.6 g, 14%, 99% ee, S). The subsequent liquor was then concentrated on rotavapour, and the third crop was obtained (0.4 g, 10 %, 97% ee, S). The residue was dissolved in MeOH (0.2 ml) under reflux, the solution was then cooled to room temperature. The D-S salt seed was added, and further recrystallisation gave the fourth crop (0.2 g, 4.5%, 99.4% ee, S).

The first crop obtained from recrystallisation (0.26 g) was treated with 48% NaOH (4.5 ml) ice water (15 ml). A total of 15 ml MTBE was used to extract out the free methylamino intermediate completely in optically pure form (0.12 g, 100%, S, $(\alpha)_D$ =(−)5.69 (c=1.16 abs. EtOH)).

d) Preparation of 1-(2-bromoethyl)-3,4-dimethoxybenzene

Triphenylphosphine (1.64 g, 6.2 mmol) was added to a solution of 2-(3,4-dimethoxyphenyl)-1-ethanol (1.027 g, 5.64 mmol) in dichloromethane (6 ml) at 0° C., followed by the dropwise addition of bromine (1.0 g, 6.2 mmol). The reaction was quenched with water after 2 hours. Usual work-up, including quenching with water after two hours, and then extracting with MTBE and then drying the organic extract obtained with $MgSO_4$, and concentrating under pressure, gave the crude product (1.468 g), which was taken directly to the next step.

e) Preparation of 2-(3,4-Dimethoxyphenyl,-5-[2-3, 4-dimethoxyphenyl, ethyl-N-methylamino]-2-isopropylpentanenitrile The optically pure methylamino intermediate from step c) above (0.203 g, 0.7 mmol), 1-(2-bromoethyl)-3,4-dimethoxybenzene (0.189 g, 0.77 mmol), and $K_2Co_3$ (0.293 g, 2.1 mmol) in acetonitrile (6 ml) were heated up to reflux for 3 days. The reaction product was then quenched with water and extracted with MTBE. The MTBE extract was acidified with 2N HC1, and further extracted with 2N HC1. The organic layer was disposed of. The combined aqueous layers were then basified with 48% NaOH, and extracted with diethyl ether. Usual work-up, including drying the organic extract using $MgSO_4$ and concentrating under reduced pressure, gave the desired product (0.30 g, 94%).

We claim:

1. A process for preparing a single enantiomer, either R or S in enantiomeric excess of about 90% or greater, of a compound having the formula $$R'-NH-(CH_2)_3-C^*(Ar)(CN)-R \qquad (I)$$

the process comprising reacting together $$R-CH(AR)-CN \text{ and } X-(CH_2)_3-A$$

to give a compound having the formula $$X-(CH_2)_3-C(Ar)(CN)-R, \qquad (II)$$

reacting compound II with $R'NH_2$ to give a compound having the formula $$R'-NH-(CH_2)_3-C(Ar)(CN)-R \qquad (III)$$

and resolving compound III into a single enantiomer thereof by reacting compound III with a chiral acid, wherein * denotes a chiral center, Ar is aryl, R and R' are each independently $C_{1-20}$ alkyl, X is a halo atom and A is a leaving group which, upon reaction of R—CH(Ar)—CN and X—$(CH_2)_3$—A, leaves X—$(CH_2)_3$—A as A.

2. The process according to claim 1, wherein R' is methyl.

3. The process according to claim 1, wherein Ar is 3,4-dimethoxyphenyl and R is isopropyl.

4. The process according to claim 1, wherein the chiral acid is selected from the group consisting of (+)-di-o,o'-toluyltartaric acid, (−)-di-o,o'-toluyltartaric acid, (+)-lithocholic acid and (R)-α-methoxy-2-(trifluoromethyl) phenylacetic acid.

5. A process for preparing a single enatiomer, either R or S, in enantiomeric excess of about 90% or greater, of a compound of the formula

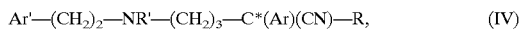
(IV)

the process comprising carrying out the process of claim 1 and reacting the product thereof with Ar'—(CH$_2$)$_2$—A', wherein * denotes a chiral center, Ar' is aryl and A' is a leaving group which, upon reaction of Ar'—(CH$_2$)$_2$—A' with the product of claim 1, leaves Ar'—(CH$_2$)$_2$—A' as A'$^-$.

6. The process according to claim 5, wherein Ar' is 3,4-dimethoxyphenyl.

7. A process for preparing a single enantiomer, either R or S, in enantionmeric excess of about 90% or greater, of verapamil, the process comprising carrying out the process of claim 3 and reacting the product thereof with Ar'—(CH$_2$)$_2$—A' wherein Ar' is aryl and A' is leaving group which, upon reaction of Ar'—(CH$_2$)$_2$A' with the product of claim 3, leaves Ar'—(CH$_2$)$_2$—A' as A'$^-$.

* * * * *

UNITED STATES PATENT AND TRADEMARK OFFICE
CERTIFICATE OF CORRECTION

PATENT NO.      : 5,910,601

DATED           : June 8, 1999

INVENTOR(S)     : Raymond McCague and Shouming Wang

It is certified that error appears in the above-identified patent and that said Letters Patent is hereby corrected as shown below:

In the Claims

<u>Column 4, line 40:</u> Delete "R-CH(AR)-CN" and insert --R-CH(Ar)--CN--.

<u>Column 4, line 56:</u> Delete " as A." and insert --as A⁻.

Signed and Sealed this

Second Day of November, 1999

Attest:

Q. TODD DICKINSON

*Attesting Officer*     Acting Commissioner of Patents and Trademarks